US00PP29898P2

(12) United States Plant Patent
Danziger

(10) Patent No.: US PP29,898 P2
(45) Date of Patent: Nov. 27, 2018

(54) ***LOBULARIA* PLANT NAMED 'DLOBUDLAVS'**

(50) Latin Name: *Lobularia maritima*
Varietal Denomination: DLOBUDLAVS

(71) Applicant: Gavriel Danziger, Beit Dagan (IL)

(72) Inventor: Gavriel Danziger, Beit Dagan (IL)

(73) Assignee: Danziger "DAN" Flower Farm (IL)

( * ) Notice: Subject to any disclaimer, the term of this patent is extended or adjusted under 35 U.S.C. 154(b) by 0 days.

(21) Appl. No.: 15/731,347

(22) Filed: May 30, 2017

(51) Int. Cl.
*A01H 5/02* (2018.01)

(52) U.S. Cl.
USPC ..... Plt./263.1

(58) Field of Classification Search
USPC ..... Plt./263.1
CPC ..... A01H 5/02; A01H 5/00; A01H 6/20
See application file for complete search history.

(56) References Cited

U.S. PATENT DOCUMENTS

PP24,516 P2 * 6/2014 Wicki-Freidl ..... A01H 5/02
Plt./263.1

PP26,092 P3 * 11/2015 Danziger ..... A01H 5/02
Plt./263.1

OTHER PUBLICATIONS

Danziger *Lobularia* Deep Lavender Stream, retrieved on Apr. 23, 2018, retrieved from the Internet at https://danzigeronline.com/variety/stream-deep-lavender/lobularia-deep-lavender-stream-flower/, 1 page. (Year: 2018).*

Lucas Greenhouses 201-2017 Supplemental Young Plant Catalog, retrieved on Apr. 23, 2018, retrieved from the Internet at http://www.lucasgreenhouses.com/_ccLib/attachments/pages/2016-2017+Supplemental+Liner+Catalog.pdf, pp. 1-6,26,48-52. (Year: 2016).*

* cited by examiner

*Primary Examiner* — June Hwu
(74) *Attorney, Agent, or Firm* — Cassandra Bright

(57) ABSTRACT

A new and distinct *Lobularia* cultivar named 'DLOBUDLAVS' is disclosed, characterized by large flowers and distinctively wide and thick foliage. Plants produce 3 different color shades within 1 inflorescence. The new variety is a *Lobularia*, normally produced as an outdoor garden or container plant.

2 Drawing Sheets

Figure 1:
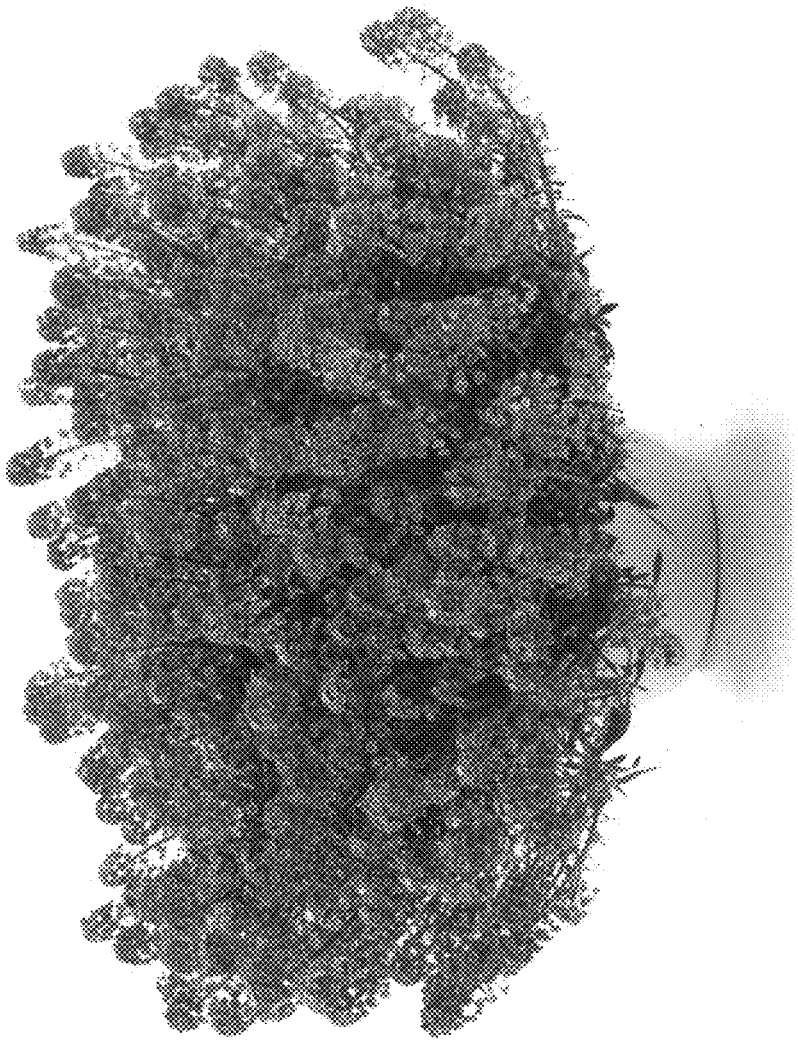

Latin name of the genus and species: *Lobularia maritima*.
Variety denomination: 'DLOBUDLAVS'.

BACKGROUND OF THE INVENTION

The new *Lobularia* cultivar is a product of chance discovery by the inventor, Gavriel Danziger, in Moshav Mishmar Hashiva, Israel. The new variety was discovered as a whole plant mutation at a research greenhouse in during October of 2013.

The parent variety is an unpatented, proprietary variety referred to as *Lobularia* 'AY-11-292'. The new variety was discovered as a naturally occurring, whole plant mutation in a small motherstock planting of the parent variety, in a research greenhouse in Moshav Mishmar Hashiva, Israel.

Asexual reproduction of the new cultivar has been performed by terminal vegetative cuttings. This was first performed at a research greenhouse in Moshav Mishmar Hashiva, Israel in December of 2013 and has shown that the unique features of this cultivar are stable and reproduced true to type in multiple successive generations.

SUMMARY OF THE INVENTION

The cultivar 'DLOBUDLAVS' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DLOBUDLAVS' These characteristics in combination distinguish 'DLOBUDLAVS' as a new and distinct *Lobularia* cultivar:

1. Large flowers.
2. Distinctively wide and thick foliage.
3. Attractive and unique inflorescence with three color shades.

Plants of the new cultivar 'DLOBUDLAVS' are similar to plants of the parent, in most horticultural characteristics, however, plants of the new cultivar 'DLOBUDLAVS' differ in the following;

1. The new variety produces larger flowers than the parent variety.
2. The new variety has a longer pedicel.
3. The new variety has larger foliage.

COMMERCIAL COMPARISON

Plants of the new cultivar 'DLOBUDLAVS' are comparable to the patented commercial variety *Lobularia* 'INLBUBLUPR' U.S. Plant Pat. No. 24,516. The two *Lobularia* varieties are similar in most horticultural characteristics; however, the new variety 'DLOBUDLAVS' differs in the following:

1. The new variety has wider leaves.
2. Flower color—plants of the new variety have more purple shades within the infloresence than this comparator.
3. Plant of the new variety have a denser form.
4. The new variety produces inflorescences with 60 to 70 flowers per inflorescence, this comparator produces inflorescences with about 50 flowers per inflorescence.

Plants of the new cultivar 'DLOBUDLAVS' can also be comparable to the patented commercial variety *Lobularia* 'DLOBU23', U.S. Plant Pat. No. 26,092. The two *Lobularia* varieties are similar in most horticultural characteristics; however, the new variety 'DLOBUDLAVS' differs in the following:

1. The new variety produces larger individual flowers. Individual flowers of the new variety are approximately 8 mm in diameter, individual flowers of this comparator are approximately 5 to 6 mm.
2. The new variety has wider leaves.
3. New variety has a more vigorous growth habit.

BRIEF DESCRIPTION OF THE PHOTOGRAPHS

The accompanying photograph in FIG. 1 illustrates in full color a typical plant of 'DLOBUDLAVS' grown in a greenhouse, in a 15 cm pot. Age of the plant photographed is approximately 7 weeks from sticking.

Figure 2:
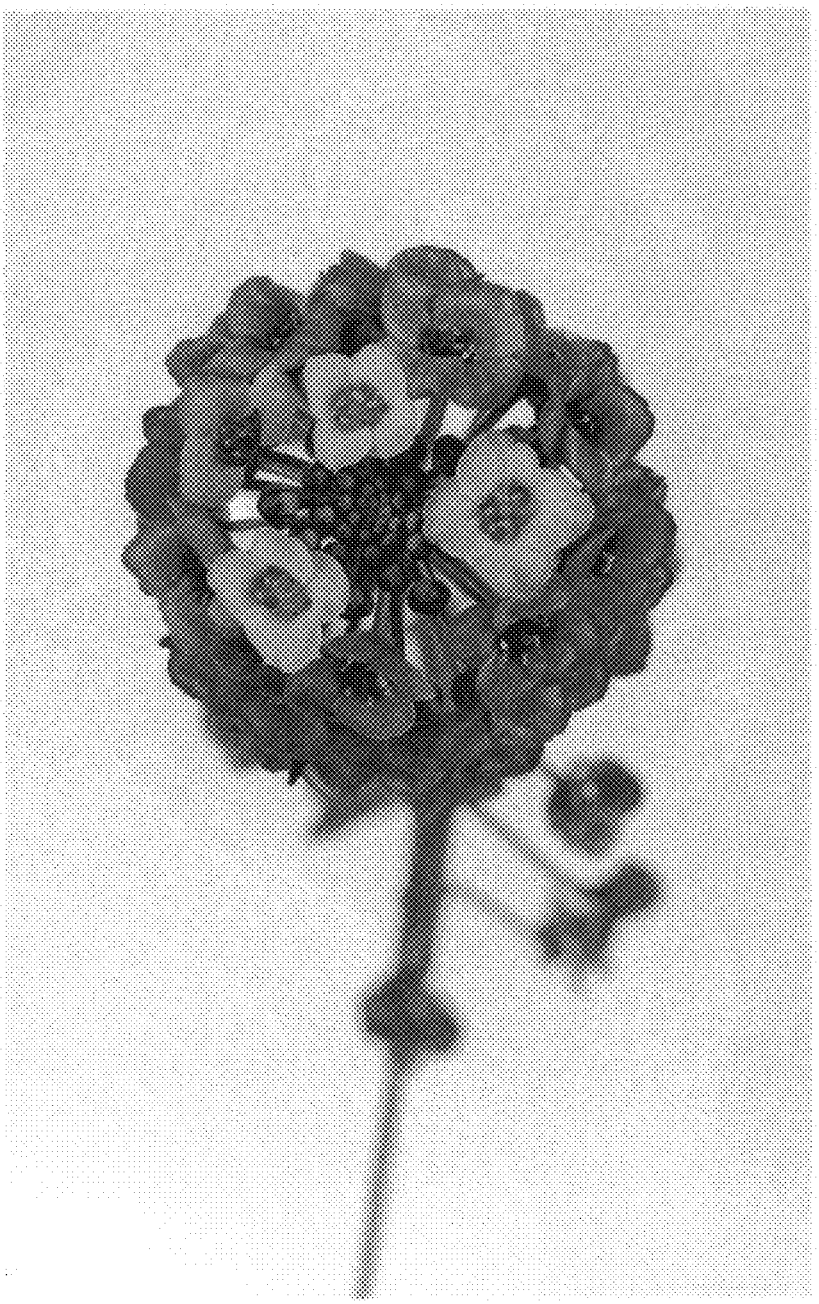

FIG. 2 illustrates a close up of the inflorescence.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DLOBUDLAVS' plants grown in the Autumn, to Spring in a greenhouse, in Moshav Mishmar Hashiva, Israel. The growing temperature ranged from 18° C. to 30° C. during the day and from 9° C. to 17° C. during the night. General light conditions are high light levels 60,000 to 90,000 Lux Measurements and numerical values represent averages of typical plant types.

Botanical classification: *Lobularia maritima* 'DLOBUDLAVS'.

PROPAGATION

Type of propagation typically used: Terminal vegetative cutting.

Time to initiate roots: 14-20 days at approximately 17° C.

Root description: Thin, fibrous, freely branching. Near RHS White 155C in color.

Time to produce a rooted young plant: Approximately 4 weeks.

PLANT

Age of plant described: Approximately 7 weeks.

Container size of the plant described: 12 cm.

Growth habit: Semi-trailing and vigorous.

Height: Approximately 9 cm.

Plant spread: Approximately 23 cm (radius).

Growth rate: Fast growing with moderate vigor.

Branching characteristics: Freely branching.

Approximate quantity of lateral branches: Approximately 4 to 5 primary lateral branches and numerous secondary and tertiary lateral branches.

Length of lateral branches: Approximately 21 cm.

Diameter of lateral branches: Approximately 0.3 cm.

Texture of lateral branches: Slightly Pubescent.

Lateral branch shape: Hexagonal in cross section.

Lateral branch strength: Strong (good).

Lateral Branch Color: Near RHS Yellow-green 144A.

Internode length: 2.5cm (average).

Number of leaves per lateral branch: Average 18.

FOLIAGE

Leaf:

*Arrangement*.—Alternate.
*Shape of blade*.—Oblanceolate.
*Average length*.—Approximately 7.5 cm.
*Average width*.—Approximately 1.3 cm.
*Apex*.—Acute.
*Base*.—Cuncate.
*Attachment*.—Sessile.
*Margin*.—Entire.
*Texture of top surface*.—Glabrous.
*Texture of bottom surface*.—Glabrous.
*Color*.—Young foliage upper side: Near RHS Green 137A. Young foliage under side: Near RHS Green 137C. Mature foliage upper side: Near RHS Green 137B. Mature foliage under side: Near RHS Green 137C.
*Venation*.—Indistinguishable from foliage blade.
*Petiole*.—Not present.

FLOWER

Bloom period:

*Natural season*.—April until June and again September to November in Moshav Mishmar, Israel.
*In commercial production, flowering begins from a rooted cutting*.—Approximately 3 to 4 weeks.

Inflorescence:

*Arrangement*.—Panicle.
*Height*.—Approximately 8 cm.
*Width*.—Approximately 3 to 3.5 cm.
*Quantity of flowers per inflorescence*.—Approximately 60 to 70 flowers.

Bud:

*Bud shape*.—Globose spherical.
*Bud length*.—Approximately 1.5 mm.
*Bud diameter*.—Approximately 1.5 mm.
*Bud color*.—Near RHS Yellow-Green 144A.
*Rate of opening*.—Individual flowers: Fully open approximately 2 to 3 days from the bud stage.

Individual flower:

*Shape*.—Cross Shaped.

*Quantity of flowers and buds per plant*.—Approximately 60 to 70 flowers and buds per inflorescence — more than 2500 flowers per plant.

*Diameter of entire flower*.—Approximately 0.8 cm.

*Depth of flower*.—Approximately 1 mm.

*Flower longevity on plant*.—Approximately 6 days.

*Persistent or self-cleaning*.—Self-cleaning.

*Fragrance*.—Sweet, honey like.

Petals:

*Length of petal*.—Approximately 4 mm.

*Width of petal*.—Approximately 4 mm.

*Apex*.—Rounded.

*Base*.—Reniform.

*Shape of petal*.—Orbicular.

*Petal margin*.—Entire.

*Petal arrangement*.—4 petals fused in a single whorl.

*Petal number*.—4.

*Petal appearance*.—Matte.

*Petal texture*.—Smooth, glabrous, upper and lower surfaces.

Color:

*Upper surface at first opening*.—Near RHS White N155C.

*Upper surface at middle stage*.—Near RHS Purple 76A.

*Upper surface at maturity*.—Near RHS Violet 83C.

*Upper surface at fading*.—Near RHS Purple-Violet N82B.

*Under surface at first opening*.—Near RHS White N155B.

*Under surface at middle stage*.—Near RHS Purple-Violet N82C.

*Under surface at maturity*.—Near RHS Violet 83B.

*Under surface at fading*.—Near RHS Purple-Violet N82A.

Note: Color is darker in cold weather and when grown outside.

Sepal:

*Number*.—4.

*Sepal appearance*.—4 sepals.

*Sepal arrangement*.—4 sepals in a single whorl.

*Sepal length*.—Approximately 2 mm.

*Sepal width*.—Approximately 1 mm.

*Sepal shape*.—Elliptic.

*Base*.—Truncate.

*Apex shape*.—Acute.

*Margin*.—Entire.

*Color*.—Near RHS Yellow Green 144A.

*Texture*.—Glabrous all surfaces.

Peduncle:

*Length*.—Approximately 2.5 cm.

*Diameter*.—Approximately 4 mm.

*Aspect*.—Straight.

*Strength*.—Strong.

*Color*.—Near RHS Yellow-Green 146B.

*Texture*.—Glabrous.

Pedicel:

*Length*.—Approximately 1.1 cm.

*Diameter*.—Approximately 0.5 mm.

*Angle*.—Approximately 90-110 degrees.

*Strength*.—Flexible, moderately strong.

*Color*.—Near RHS Yellow-green 146A.

*Texture*.—Glabrous.

Reproductive organs:

*Number of pistils per flower*.—1.

*Pistil length*.—Approximately 1 to 1.5 mm.

*Stigma shape*.—Rounded to broadly spreading.

*Stigma color*.—Near RHS Yellow-Green 144B.

*Style color*.—Near RHS Yellow-Green 144B.

*Style length*.—Less than 0.5 mm.

*Ovary color*.—Near RHS Yellow-Green 144A.

*Stamens quantity*.—6.

*Stamen length*.—2 mm.

*Filament length*.—About 1.4 mm.

*Filament color*.—Near yellow-Green 145D.

*Anther shape*.—Elliptic.

*Anther size*.—About 0.5 mm in length and width.

*Anther color*.—Near RHS Yellow 7B.

*Pollen color*.—Near RHS Yellow 7A.

*Pollen quantity*.—Abundant.

OTHER CHARACTERISTICS

Disease resistance: Neither resistance nor susceptibility to normal diseases of *Lobularia* has been observed. Typical diseases include *Botrytis, Plasmodiophora brassicae* (Alyssum clubroot), *Plasmopara* spp., and various species of *Fusarium, Pythium, Phytophthora*, and *Rhizoctonia*.

Drought tolerance and cold tolerance: Plants of the new *Lobularia* have been noted to have good tolerance at temperatures from 1° C. to 38° C. and also tolerate rain and windy conditions.

Color and shape of fruits and seeds: The fruits and seeds are elliptical and flat, less than 1 mm long and 1.0 mm wide. The color of the mature seed is near RHS Grey-orange 165A.

What is claimed is:

1. A new and distinct cultivar of *Lobularia* plant named 'DLOBUDLAVS' as herein illustrated and described.

* * * * *